(12) United States Patent
Gingsjo

(10) Patent No.: US 8,600,473 B2
(45) Date of Patent: Dec. 3, 2013

(54) FETAL ELECTRODE ASSEMBLY AND FETAL ELECTRODE

(75) Inventor: Anders Lars Gingsjo, Kungsbacka (SE)

(73) Assignee: Neoventa Medical AB, Molndal (SE)

( * ) Notice: Subject to any disclaimer, the term of this patent is extended or adjusted under 35 U.S.C. 154(b) by 201 days.

(21) Appl. No.: 13/147,967

(22) PCT Filed: Feb. 5, 2010

(86) PCT No.: PCT/EP2010/000731
§ 371 (c)(1),
(2), (4) Date: Aug. 4, 2011

(87) PCT Pub. No.: WO2010/089133
PCT Pub. Date: Aug. 12, 2010

(65) Prior Publication Data
US 2011/0295097 A1    Dec. 1, 2011

(30) Foreign Application Priority Data

Feb. 6, 2009    (GB) .................................... 0902069.4

(51) Int. Cl.
*A61B 5/0448*    (2006.01)
(52) U.S. Cl.
USPC .......................................... 600/376; 600/511
(58) Field of Classification Search
USPC ................................................ 600/376, 511
See application file for complete search history.

(56) References Cited

U.S. PATENT DOCUMENTS

| | | | |
|---|---|---|---|
| 3,827,428 A | 8/1974 | Hon et al. | |
| 4,320,764 A | 3/1982 | Hon | |
| 4,577,635 A | 3/1986 | Meredith | |
| 4,686,996 A * | 8/1987 | Ulbrich | 600/376 |
| 5,183,043 A | 2/1993 | Band et al. | |
| 5,215,090 A | 6/1993 | Hon et al. | |
| 5,222,498 A | 6/1993 | Neward | |
| 5,388,579 A | 2/1995 | Dowd et al. | |
| 5,423,314 A | 6/1995 | Schmid | |
| 5,662,103 A | 9/1997 | Smith et al. | |
| 5,671,736 A | 9/1997 | Pettit et al. | |
| 6,201,978 B1 | 3/2001 | Buschmann | |
| 7,016,716 B2 | 3/2006 | Rall et al. | |

FOREIGN PATENT DOCUMENTS

| | | |
|---|---|---|
| CA | 2128766 A1 | 1/1996 |
| DE | 42 28 351 C1 | 4/1994 |
| EP | 0 113 253 A2 | 11/1984 |
| GB | 2467648 | 4/2011 |
| WO | 00/36975 A1 | 6/2000 |
| WO | 2008/109606 A2 | 9/2008 |

OTHER PUBLICATIONS

International Search Report for Serial No. PCT/EP2010/000731 dated Mar. 19, 2010.
Search Report for GB Serial No. GB0902069.4 dated May 28, 2009.
Search Report for GB Serial No. 1001981.8 dated May 29, 2010.

* cited by examiner

*Primary Examiner* — Lee S Cohen
(74) *Attorney, Agent, or Firm* — McCormick, Paulding & Huber LLP

(57) ABSTRACT

An electrode assembly comprising a fetal electrode (1) that is connected to a drive tube (31) by a torque limiting connection (30). The connection allows the drive tube to separate from the electrode hub once a predetermined torque has been reached. The electrode hub is also provided with a deflection surface (9) that deflects the drive tube away from the fetal electrode into the hand of the operator, as rotation of the drive tube continues beyond the point of disconnection. Features are also provided to make the fetal electrode more compact and to optimise the fECG signal recorded on the electrode wires (5, 9).

22 Claims, 11 Drawing Sheets

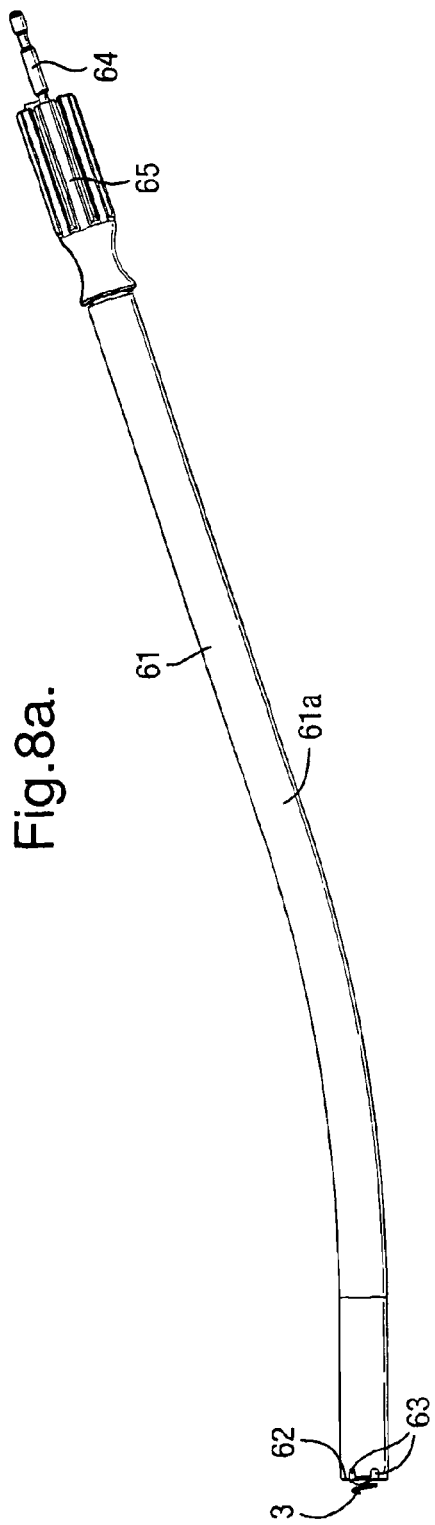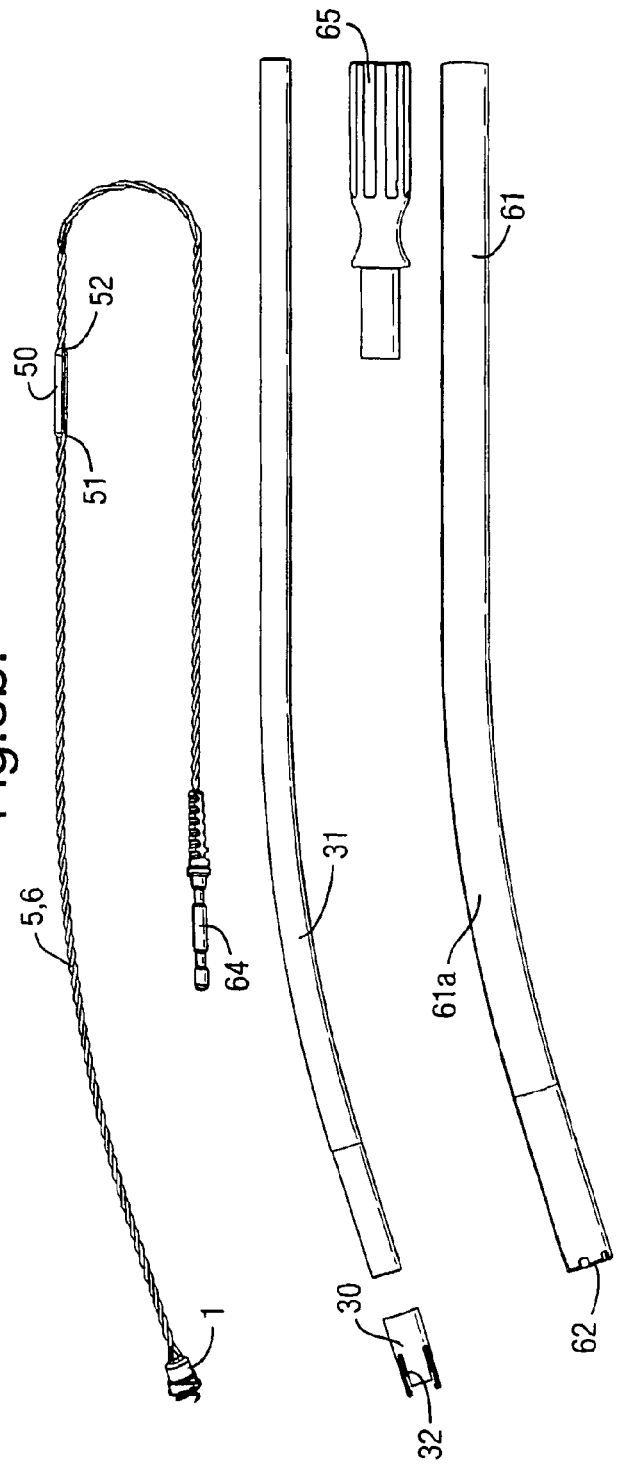

FETAL ELECTRODE ASSEMBLY AND FETAL ELECTRODE

CROSS REFERENCE TO RELATED APPLICATIONS

This application is entitled to the benefit of and incorporates by reference essential subject matter disclosed in International Patent Application No. PCT/EP2010/000731 filed on Feb. 5, 2010 and Great Britain Patent Application No. 0902069.4 filed Feb. 6, 2009.

FIELD OF THE INVENTION

The present invention relates to an improved fetal electrode assembly. The assembly includes a new fetal electrode with an improved electrode hub design which is for attachment to a fetus, for example, on the scalp of the fetus. The new fetal electrode is intended for monitoring fetal ECG, in particular aimed towards, but not limited to, ST-analysis.

BACKGROUND OF THE INVENTION

The importance of reducing signal noise in a fetal ECG signal is described in WO-A-00/36975. Changes in the ST interval of the fetal Electrode Cardiogram (ECG) are known to reflect the stress of the fetal heart during labour. Lack of oxygen may cause an ST rise with increased ST segment and T-wave amplitude, the appearance of so-called bi-phasic ST changes with an ST segment having a negative slope, and the appearance of negative T-waves. The electrode is mounted on the longitudinal axis of the fetus in order to be sensitive to the ECG wave form changes, usually on the scalp of the fetus as this is the part which should present first.

Fetal scalp electrodes generally tend to be of the spiral electrode type, and these have not changed significantly since the beginning of the 1970's. An example is shown in U.S. Pat. No. 3,827,428. It comprises a cylindrical body, which is approximately 1 cm long and 0.5 cm in diameter, with a spiral electrode exiting from one end, usually in the form of a single helix requiring a 360° turn for full insertion. The height of the spiral electrode is chosen so that it should not penetrate into the parietal bone of the fetus whilst providing an electrode that is as long as possible to record a strong signal. In some arrangements, the electrode may have two helical prongs and require only a turn through 180° in order to locate the electrode properly. At the other end of the cylindrical housing, a plate electrode extends axially and projects into the amniotic fluid to take a reference or ground potential. Using a slot in the end of an applicator tube, this plate electrode can be driven to screw the device into the fetus. In addition to double helix designs, other designs such as the Copeland style electrode are available, but the single helix design is by far the most widely used and is the fetal electrode that provides the most consistent ECG trace.

There are documented clinical problems associated with the design of the fetal spiral electrode. One is that fetal scalp hair and tissue becomes entrapped between the electrode wire and the plastic body of the electrode hub, which can make it both difficult to attach properly and to remove.

Another associated problem is that the fetal electrode may unscrew itself due to the pitch of the spiral wire and the slippery surface of the hub, especially in the presence of vernix caseosa on the fetal scalp and amniotic fluid. One solution proposed in U.S. Pat. No. 5,222,498 suggests preventing spontaneous unwinding by incorporating barbs on the hub surface. However, these are generally disliked and are likely to damage the fetal epidermis during electrode removal.

CA-A-2128766 provides a solution in part to the problem. In that device, the spiral electrode is sunken into a recess within the end of the cylindrical housing. The recess helps to trap tissue and thereby prevent unwinding of the fetal electrode. However, in practice there are still problems with the retention of the fetal electrode, as well as difficulties within the manufacturing phase through complicated and expensive tooling.

Midwives have also described vaginal lacerations on patients, which they believe to originate from the sharp reference part of the fetal scalp electrode. The reference electrode is usually produced by punching, which can leave sharp edges on one side even after the finishing process. The current shape of the electrode hub also provides a long lever which can be overturned during labour, resulting in the sharp spiral tip being pressed out from the fetal epidermis and possible vaginal lacerations.

The fetal scalp electrode ECG (fECG) signal quality is highly dependent on the penetration of the spiral wire electrode into the fetal epidermis. It has been found that if any part of the spiral wire should be exposed to the environment outside the fetal epidermis then this can greatly affect signal quality. This is especially noticeable in the fECG-trace when the scalp electrode spontaneously unwinds. It can lead to a substantial loss of signal amplitude, for example, a loss of 80% of the signal amplitude (i.e. a reduction to one fifth of the signal amplitude) has been observed in real recordings.

FIG. 1 shows the trace from a real case where a poorly applied fetal electrode later fell off the scalp of the fetus. The traces in the far left box show the initial averaged ECG complexes and the corresponding CTG (CardioTocoGram) trace. With the poor application, the QRS-amplitude is around 100 µV. The boxes on the right show the situation about one hour later when the electrode has been correctly re-applied. As can be seen, the QRS-amplitude is then instead 290 µV. Tests have also been conducted on adults in a bath tub filled with water containing 0.9% NaCl, showing an initial loss in the fECG signal amplitude of a factor of two for the first 90° of unwinding of the spiral electrode. The resulting ECG traces for a near perfectly applied fetal electrode, one which has been unscrewed a quarter of a turn, and one which has been unscrewed half of a turn, are shown in FIG. 2. The total drop in QRS-amplitude was from 210 µV to 70 µV when the fetal scalp electrode was unwound by half a turn. At this point, part of the spiral electrode would be visible to an observer on inspection.

A major factor in determining whether a fetal electrode is applied well, which in turn helps to keep it from unwinding, is that enough, but not too much torque is used during the application. This can be difficult to achieve in practice because the drive tubes of the currently available fetal scalp electrodes are quite soft in order to protect the fetus from the fetal electrode being overtightened. This softness results in poor tactile feedback to the midwife which in turn can lead to uncertainty in knowing whether the electrode is properly attached. Despite this and the problems mentioned above, the design of the electrode assemblies that are in every day use have hardly changed from the arrangement shown in U.S. Pat. No. 3,827,428.

A few more complex solutions have been proposed for the applicating devices, incorporating a number of mechanical elements in order to limit the maximum torque that is applied during insertion. For example, in U.S. Pat. No. 4,577,635 the electrode assembly is provided with a torque limiting device in the form of a helical spring which is rotatable with the fetal electrode at low torque but which is arranged to disengage from frictional driving contact at the torque limit. This has allowed for a stiffer drive tube. U.S. Pat. No. 5,388,579 is a further example where attempts have been made to provide a clutch within the drive mechanism in order to be able to limit the amount of torque that is applied and to allow the use of a stiffer drive rod.

When the fetal electrode comes loose, in addition to loss of the fECG signal amplitude there is also an increase in the competing low frequency (base line) noise through the exposed spiral wire electrode being subjected to relative feto-maternal movement and varying amounts of amniotic fluid. In U.S. Pat. No. 5,183,043, it is recognised that noise originating from relative feto-maternal movement can be reduced and low frequency electrical activity from the fetus can be picked up with better accuracy by providing a chloridized silver coating on a Copeland-type electrode, allowing consistent waveforms (P, QRS and T waves) of the cardiac cycle to be more easily identified. A coating of a non-conducting varnish may be provided on regions without the chloridized silver layer. This would include the tip of the Copeland electrode, which in use projects outside the fetal epidermis and therefore must be isolated in order to obtain full fECG signal amplitude. It has been shown that the resulting amplitude of a Copeland electrode can be as little as half of that of a conventional single helix electrode.

Although U.S. Pat. No. 5,183,043 suggests that a chloridized silver layer may be used in conjunction with other types of electrode, further experiments using such a chloridized silver coating on a traditional helix electrode has showed no difference compared with a plain stainless steel electrode, since the main source of noise, which originates from muscular activity, can only be made negligible by increasing the amplitude of the ECG signal if the surface of the stainless steel has been subjected to a process of passivation. Here, passivation is the chemical treatment of a stainless steel with a mild oxidant, such as a nitric acid solution, for the purposes of enhancing the spontaneous formation of a protective passive film. For fECG signals this means that unwanted surface corrosion dependent electrical noise is minimized due to the formation of a thin transparent film of inert chromic oxide.

The increased fECG signal amplitude from a spiral electrode which has been totally embedded in the fetal epidermis, is attributed to the difference in the electric volume conductivity in the interface of the fetal epidermis and the surrounding maternal tissue and amniotic fluid. The lower electrical volume conductivity present in this interface results in an increased ECG voltage potential, if measured exclusively within the fetal epidermis. In addition, the presence of the isolating vernix caseosa on the fetal head contributes to this effect. As fetal tissues and the vernix caseosa have the lowest volume conductivity and the amniotic fluid has the highest, it is important to keep the scalp electrode spiral entirely separated from the amniotic fluid.

Attempts have been made to provide a fetal scalp electrode design which keeps the spiral electrode separated from the amniotic fluid, for example, as shown in U.S. Pat. No. 7,016,716. However, the relatively large diameter of the sensor makes it more difficult to apply in the first stage of labour as well as increasing manufacturing costs, and therefore this type of fetal electrode has not been adopted for common use.

Thus, it can be seen that there is an overriding technical problem of how to improve the design of fetal scalp electrodes so that the ECG trace quality can be optimised.

SUMMARY OF THE INVENTION

In the present invention, the design of the hub of the fetal electrode and the assembly for fitting the fetal electrode has been improved in order to optimise the ECG trace quality. In particular, the present invention addresses this technical problem in three ways, namely (i) modifications to improve the insertion of the spiral electrode into the scalp of the fetus so that a reliable and correct connection is made, (ii) modifications to improve the retention of the fetal electrode so that, as far as possible, it does not unwind during use, and (iii) modifications to the fetal electrode in order to provide further improvements to the signal quality in the unlikely event there is any unwinding of the fetal electrode.

According to a first aspect, there is provided an electrode assembly comprising a fetal electrode and a drive tube, the fetal electrode having an electrode hub with a spiral wire electrode provided on one end, the fetal electrode being connected to the drive tube by a torque limiting connection, the connection allowing the drive tube to separate from the electrode hub and to continue to turn with respect to the electrode hub once a predetermined torque has been reached, wherein the electrode hub is provided with a deflection surface to deflect the drive tube in a direction away from the end of the hub with the spiral wire electrode as rotation of the drive tube continues beyond the point of disconnection.

The advantage of such an arrangement is that the deflection of the drive tube can be felt by the midwife or person installing the fetal electrode as a small push back into the hand, providing positive feedback that a correct and reliable connection has been made with the scalp of the fetus. In addition, the torque limiting connection guarantees that a correct amount of torque is applied to the electrode hub, further improving the reliability of the connection and also ensuring that such a reliable connection is reproducible by different operators working under different conditions. Preferably the deflection surface also deflects the drive tube sufficiently to prevent reconnection upon further rotation of the drive tube.

In one embodiment, the present invention can be seen to provide a fetal electrode comprising a substantially cylindrical electrode hub with a spiral wire electrode extending from one end, wherein the surface of the electrode hub is provided with formations for connecting to an end of a drive tube to drive the electrode hub about an axis of rotation, the formations providing a positive connection for transmitting drive up to a limited level of torque, and wherein the electrode hub also includes a deflection surface in the form of a track which is for deflecting the drive tube in an axial direction away from the end of the electrode hub having the spiral wire electrode once the torque limiting connection has become disconnected.

Preferably the torque limiting connection comprises longitudinally extending prongs on the drive tube which engage with recesses formed in the electrode hub. Such prongs provide the advantage that they hold the fetal electrode on the end of the drive tube until it has been properly fitted to the fetus. This prevents harm to the mother or fetus through the fetal electrode becoming separated too soon. Preferably there are two or more (e.g., three or four) flexible prongs on the end of the drive tube, each having a retaining lug which is adapted to lock into a recess provided on the electrode hub, to retain the fetal electrode until the predetermined torque has been reached. The recesses may include a slopped edge at one side to allow the lug to escape from the recess on application of excessive torque via the drive tube. The recesses may be curved, for example in the form of semi-spherical hollows, but more preferably they are substantially rectangular in configuration in order to provide drive faces, and the lugs on the drive tube would be of a corresponding form. The prongs are sufficiently flexible for the lug to break free from the recess once the predetermined torque has been reached, for example through the prongs being deflected outwardly in a radial direction of the electrode hub. Preferably the end of each prong abuts against a step on the electrode hub in order to transmit longitudinal forces, for example, pushing forces as the midwife installs the fetal electrode. Two or more prongs allow these forces to be distributed uniformly around the hub, ensuring a correct fitting of the hub on the fetus.

The comparatively simple torque limiting connection of the preferred embodiment described above is also advantageous when used in conjunction with other types of electrode hub, for example, electrode hubs not necessarily including a deflection surface.

Thus viewed from another aspect, the present invention can be seen to provide an electrode assembly comprising a fetal electrode and a drive tube, the fetal electrode having an electrode hub with a spiral wire electrode provided on one end, the fetal electrode being connected to the drive tube by a torque limiting connection, the connection allowing the drive tube to separate from the electrode hub and to continue to turn with respect to the electrode hub once a predetermined torque has been reached, wherein the torque limiting connection comprises longitudinally extending prongs on the drive tube which engage with recesses formed in the electrode hub. The prongs and recesses of the torque limiting connection may have any of the preferred features mentioned above or elsewhere in this specification, for example, there may be two, three or four prongs, each provided with a retaining lug at a distal end thereof for interlocking engagement with a recess in the electrode hub.

It is also envisaged that other forms of torque limiting connection can be used in conjunction with a deflection surface, for example, prongs gripping projections, a coil spring device, or other clutch mechanism, so long as the connection will break reliably at a predetermined level of torque. Also preferably there is just a single spiral wire electrode extending from a contact face of the electrode hub, because this is considered to provide a more reliable connection. However the torque limiting connection and new hub design, e.g., incorporating a deflection surface and other novel features, could conceivably provide advantages when used in conjunction with two or even further spiral wire electrodes, and therefore such arrangements with more than one spiral wire electrode are also envisaged within the present invention.

Preferably the deflection surface, e.g., the track, is inclined with respect to the axis of the electrode hub. In one embodiment the track is inclined between 40 and 80° to the axis of rotation, more preferably greater than 60°, and most preferably inclined at around 70° (for example, ±5°) to the axis, which is equivalent to an incline of 20° to the end of the hub which contacts the fetus. 70° to the axis is advantageous because it provides the optimum amount of feedback to the midwife without driving the fetal electrode in further. In one embodiment the track preferably follows a path of constant pitch around a portion of the circumferential periphery of the hub. Preferably, two (or more) tracks are provided, one for each prong on opposite sides of the hub, in order to provide a uniform reaction force to the face of the hub contacting the fetus. Preferably the track is in the form of a spiral ramp which is stepped into the outer circumferential surface of the electrode hub. The width of the track may correspond to the depth of the retaining lug provided on the prong. The track may extend from the edge of one of the recesses so that once the prong breaks free from the recess, it is guided by the track, displacing the prong axially as the drive tube turns with respect to the electrode hub. Preferably an initial portion of the track extends over the edge of the recess that is closest to spiral wire electrode, so that as soon as the retaining lug starts to break free of the recess its distal edge urges against and is guided by the track.

Preferably the track leads onto a section of the hub with a narrower diameter to allow the end of the drive tube to disengage properly from the fetal electrode. In one embodiment a sloped surface in the form of a ramp extending axially is provided to lead onto this region of narrower diameter. This too provides feedback to the operator to help gauge when the fetal electrode is properly fitted on the fetus and the drive tube has disconnected.

The face of the electrode hub which contacts the fetus (the contact face) is preferably profiled to optimise the installation procedure and to ensure that a reliable fixing is made.

For example, the contact face preferably includes a flat, radially extending, contact surface, which extends under the spiral wire electrode and is substantially perpendicular to the axial direction to provide a stop which the operator can feel. Preferably the spiral wire electrode projects out of the hub at a position spaced away from the flat contact surface, i.e., spaced above in the axial direction, to ensure the spiral wire electrode is fully inserted before the flat contact surface is brought into firm engagement with the tissue of the fetus.

Such a novel contact surface, when provided on an electrode hub is advantageous in its own right because of the tactile feedback it provides to the mid-wife when applying the fetal electrode.

Accordingly, viewed from a further aspect there is provided a fetal electrode comprising a substantially cylindrical electrode hub having a spiral wire electrode projecting from one end thereof, said end defining a surface that is intended to contact the fetus, wherein the fetal contact surface is asymmetrical and includes a wall extending in an axial direction of the electrode hub, the wall dividing the fetal contact surface into a raised region and a lower region, the lower region providing a surface which extends substantially perpendicularly to the wall, and wherein the spiral wire electrode projects from the electrode hub by protruding from the wall at a position above the lower region. The wall and the substantially perpendicular surface of the lower region provides a rotational stop for the fetal electrode. The two regions may each represent an approximate semi-circular area. The fetal electrode may also include any of the preferred features described above or elsewhere in this specification.

A hollow, preferably in the form of a groove, more preferably a transverse groove, for example, extending substantially perpendicularly to the spiral wire electrode as it exits the hub body, may be provided beneath the spiral wire electrode. The hollow can grip fetal tissue to prevent the fetal electrode becoming separated from the fetus, and this works particularly well when the hollow is formed as a transverse groove, since then the line of pressure on the tissue trapped underneath the spiral wire is substantially perpendicular to line of grip provided by the transverse groove. A groove also provides a passage for vernix caseosa to escape from under the contact face, again helping to ensure the spiral wire electrode is properly inserted.

From the hollow or groove, a wall may extend in an axial direction up to where the spiral wire electrode exits the hub. This axially extending wall, together with the radially extending flat contact surface, provides a substantially right angled junction at the base of the spiral wire electrode to abut against the fetal tissue. This feature provides a positive stop when screwing in the fetal electrode, giving feedback to the midwife or operator, so that the spiral wire electrode is fully inserted but the fetal electrode is not overtightened. The groove profile also helps to retain it in position as fetal tissue will tend to expand into the groove and be gripped by the electrode hub.

The combination of the radially extending surface, the wall and the groove together provide a novel contact face profile, which not only helps to ensure a reliable and reproducible connection, the arrangement is also less likely to entrap hair and tissue in such a way that makes the fetal electrode difficult to remove when it needs to be taken off, as can be a problem with the prior art fetal electrodes.

In one embodiment therefore, there is provided a fetal electrode comprising:
a substantially cylindrical electrode hub;
a spiral wire electrode exiting from one end of the electrode hub for application to a fetus, wherein the surface of the electrode hub which contacts the fetus is provided with a groove, the groove extending across the contact surface beneath a base portion of the spiral wire electrode, and the groove extending transversely to the direction of the base portion of the spiral wire electrode as it exits the electrode hub.

Preferably the remainder of the material forming the contact face, which supports the base of the spiral wire electrode, is formed into a gently peaked surface to press into the fetal epidermis without harming the fetus. This profile also helps to resist accidental unwinding of the fetal electrode.

To create a bipolar device, a reference or ground electrode is provided on the end of the electrode hub opposite the spiral wire electrode and is isolated therefrom. This reference electrode may be in the form of a disc extending perpendicular to the axis of rotation and forming the end of the hub body, or more preferably is in the form of a cylindrical collar wrapped around the hub at the end opposite the spiral wire electrode. This has the advantage of providing a more compact arrangement than the upright plate-like reference electrode arrangements on conventional fetal scalp electrodes (where the plate-like electrode also serves as a spade connection to the drive tube). The lower profile design reduces the likelihood of the fetal electrode being levered out of the fetal epidermis and harming the fetus or mother. In preferred embodiments, the cylindrical electrode is made from a coiled wire. This has the advantage that a wire can be welded to a stub in the form of an end of the coiled wire, improving the likelihood of a good connection. It also means that the weld can be located in a region that is later enclosed by plastic material during a moulding operation. Any damage to the outer surface of the reference electrode from the welding will be hidden deep within the plastic hub and therefore will not affect the electrical low noise capabilities of the fetal scalp electrode. In addition, the conductive part of the electrical wire is not usually made out of the same inert material as the reference electrode, and therefore it is better to encapsulate this as far as possible within the plastic material of the hub. Any failure of these parts potentially results in excessive noise in the signal and potentially could lead to a false trace.

In one embodiment, the height of the fetal electrode excluding the spiral is reduced to less than 10 mm, preferably equal to or less than 8 mm, and more preferably around 7 mm (±0.5 mm) or less. This compares favourably to conventional fetal electrodes which tend to be around 12 mm tall excluding the spiral wire. Preferably the contact face of the hub is also slightly wider than the conventional fetal electrodes. In one embodiment the contact face is wider than 6.5 mm, more preferably at around 7.5 mm (±0.5 mm). This compares to a width of 5.5 mm for a conventional fetal electrode. The lower profile and larger base area, prevents the fetal electrode from overturning due to an excessive long lever of an extended electrode hub. An overturned fetal electrode during labour might result in the sharp spiral tip being pressed out from fetal epidermis, resulting in vaginal lacerations. It also means that a spiral wire electrode of the same diameter is more shielded from causing harm by the larger base area, in the event that the fetal electrode does become displaced.

Although a twin helix could be provided, preferably the fetal electrode has only a single spiral wire electrode extending from the contact face of the hub, and preferably this single spiral electrode extends through about 360° (for example, ±45°, or more preferably ±20°), so that one complete turn of the drive tube should ensure correct insertion of the electrode once contact with the fetus is made. Such a single spiral electrode reduces the likelihood of the fetal electrode partially unwinding or disconnecting compared to a twin helix hub that requires only half a turn.

The base of the spiral wire electrode may include an extra bend to provide a small section which extends substantially perpendicularly to the hub axis (i.e., zero pitch) or may even extend towards the contact face of the hub (i.e., a negative pitch) to grip, in a controlled way, the fetal tissue between the spiral electrode wire and the contact face of the hub. Such an arrangement can help to counteract spontaneous unscrewing of the fetal electrode. This small section may extend over the longitudinal groove and may be between 1 to 2 mm in length. It is preferably formed during a post-moulding production step.

As is usual for fetal scalp electrodes, a pair of wires project from the end of the electrode hub that is opposite the spiral wire electrode. However, the present inventors have recognised that the weight of the electrical leads can also lead to the fetal electrode unscrewing. Consequently in preferred embodiments, lighter weight and more flexible leads are used than is currently standard. This has further reduced the likelihood of the fetal electrode unwinding and the fECG signal amplitude dropping.

In one preferred embodiment, the material forming the body of the electrode hub, which is an insulating material, extends a distance along the spiral wire electrode in order to insulate the base of the spiral wire electrode from the amniotic fluid should the fetal electrode start to unwind. This helps to ensure that the fECG signal amplitude is maintained at a maximum level. In embodiments where the hub body is formed by injection moulding, the coating of the base of the spiral wire electrode can, advantageously, be carried out during the one moulding step. In addition, preferably the base of the spiral wire electrode is formed as a straight section which then leads into the helix of the spiral. This has the advantage that it is easier to coat the base of the spiral wire electrode with insulating material, such as the material of the hub body during the injection moulding step because it allows the mould halves to come together and to separate easily. It also means that the exit of the spiral wire electrode from the hub body can be more central and this has benefits in terms of making it less likely for the wire to skid off the target area during the initial moments of inserting the spiral wire electrode. It also helps to resist unwinding of the fetal electrode by moving the point at which the unwinding forces act towards the axis and so minimises the moment of the forces. In addition during removal of the fetal electrode or as a result of forces on the fetal electrode during labour, this base region of the spiral electrode will not become stretched and therefore there is less risk of the spiral electrode becoming stuck in the parietal bone and thereby harming the fetus.

Benefits can also be obtained by having a 'kinked' straight section, the base of which includes the insulating material. That is to say the straight section may be straight when viewed from above along the axis of the electrode hub, allowing the two mould halves to come together easily, but it may appear kinked when viewed side on from a point perpendicular to the hub axis. This kink can allow a region of substantially zero pitch (i.e., the wire extends perpendicularly to the hub axis for a short region) or even negative pitch (i.e., the wire descends towards the contact surface for a short region before forming the spiral), in order to provide a form which resists unwinding of the fetal electrode. The kink in the electrode wire could be formed during the step of removing waste material leftover from the injection mould channels.

In accordance with a further aspect, there is provided a fetal electrode comprising an electrode hub having a spiral wire electrode exiting from one end, wherein a base portion of the spiral wire electrode, where it exits the electrode hub, is formed as a straight section of wire and includes a coating of an insulating material for at least part of its length.

Preferably the electrode assembly of the fetal electrode and drive tube further includes a guide tube, the guide tube being of a diameter and length to fit over the drive tube and support it during positioning of the fetal electrode on the fetus, wherein a distal end of the guide tube has a circumferential edge for contacting the fetus which is crenulated. The gaps or notches provided by the crenulations allow vernix caseosa to escape from under the contact face of the fetal electrode and provide grip on the fetal tissue against the rotation of the drive tube and fetal electrode, to thereby improve the control and fitting of the fetal electrode. This feature of the crenulated end of the guide tube is advantageous in its own right independently of the other features, such as the deflection surface on the hub, the torque limiting connection and the new electrode hub design.

Accordingly, from another aspect there is provided an electrode assembly comprising a fetal electrode, a drive tube connectable to the fetal electrode for driving the fetal electrode, and a guide tube housing the drive tube and fetal electrode assembly, wherein a distal end of the guide tube has a circumferential edge for contacting the fetus which is crenulated. The electrode assembly may include any of the preferred features described above or elsewhere in this specification.

BRIEF DESCRIPTION OF THE DRAWINGS

Certain preferred embodiments of the present invention will now be described by way of example only and with reference to the accompanying figures, in which:

FIG. 8a illustrates a perspective view of an electrode assembly in its ready to use configuration;

FIG. 8b illustrates an exploded view of the components shown in FIG. 8a;

DETAILED DESCRIPTION OF THE PREFERRED EMBODIMENTS

Figure 1:
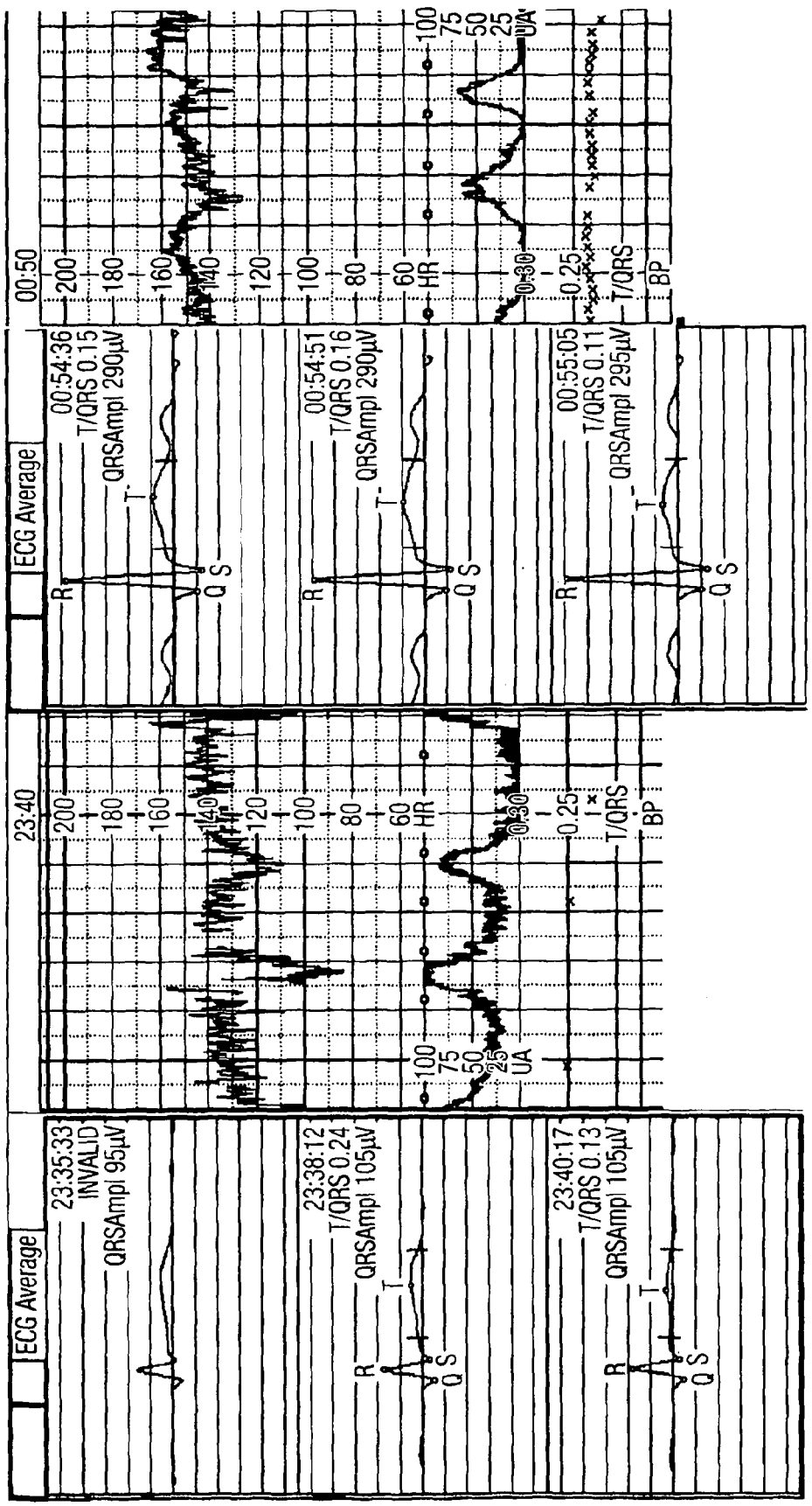
FIG. 1 shows a fECG-trace from a real case where a poorly applied fetal electrode later fell off the scalp of the fetus and a fECG trace after the electrode had been reapplied.

The left hand side of FIG. 1 illustrates a set of ECG traces for a real case where the fetal electrode eventually fell off the fetus. The left hand boxes show the initial averaged ECG complexes and the corresponding CTG trace. With the poor application, the QRS-amplitude is around 100 μV. The boxes on the right display the situation about one hour later when the electrode has been adequately re-applied. The QRS-amplitude is then instead about 290 μV, an improvement of three times on the earlier trace. Thus the importance of having a correct and reliable fitting of the fetal electrode is apparent.

Figure 2:
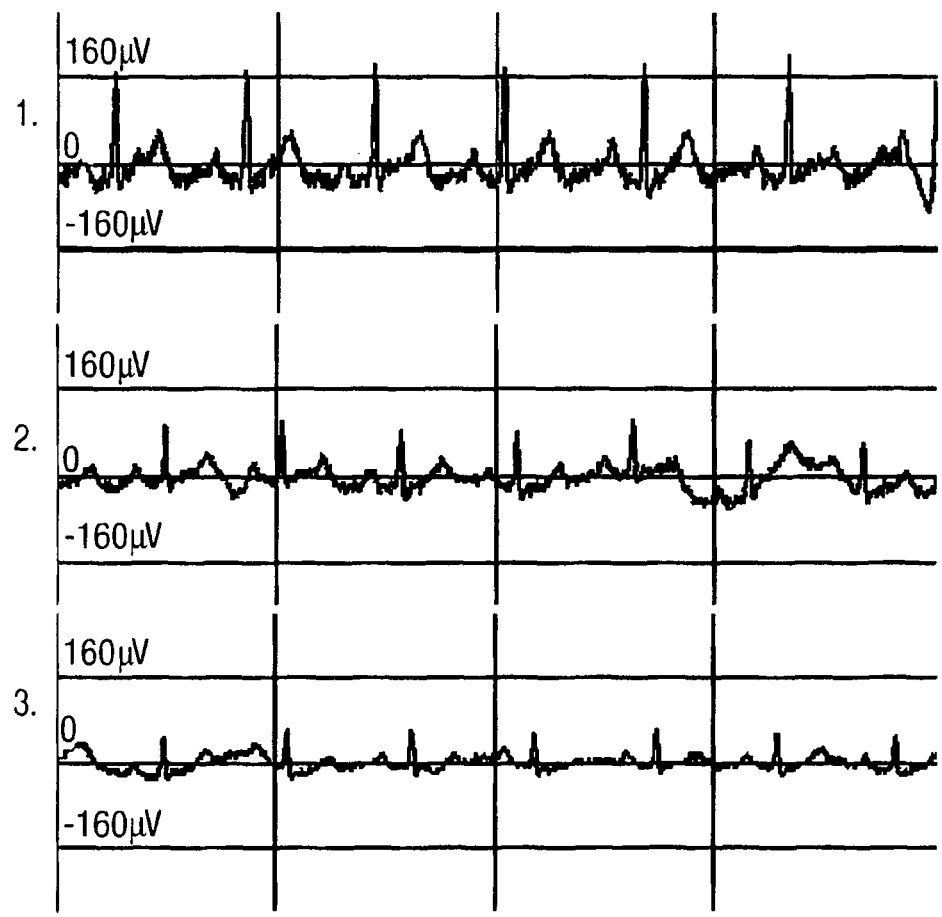
FIG. 2 illustrates traces for the resulting ECG when a fetal scalp electrode is near perfectly applied, unscrewed quarter of a turn, and unscrewed half of a turn.

FIG. 2 illustrates the resulting ECG traces for a fetal scalp electrode which in the first trace, has been near perfectly applied, in the second trace has been unscrewed one quarter of a turn, and in the third case has been unscrewed half of a turn. The reduction in the amplitude of the fECG signals as a result of the fetal scalp electrode unwinding, can be clearly seen from the traces.

Figure 3:
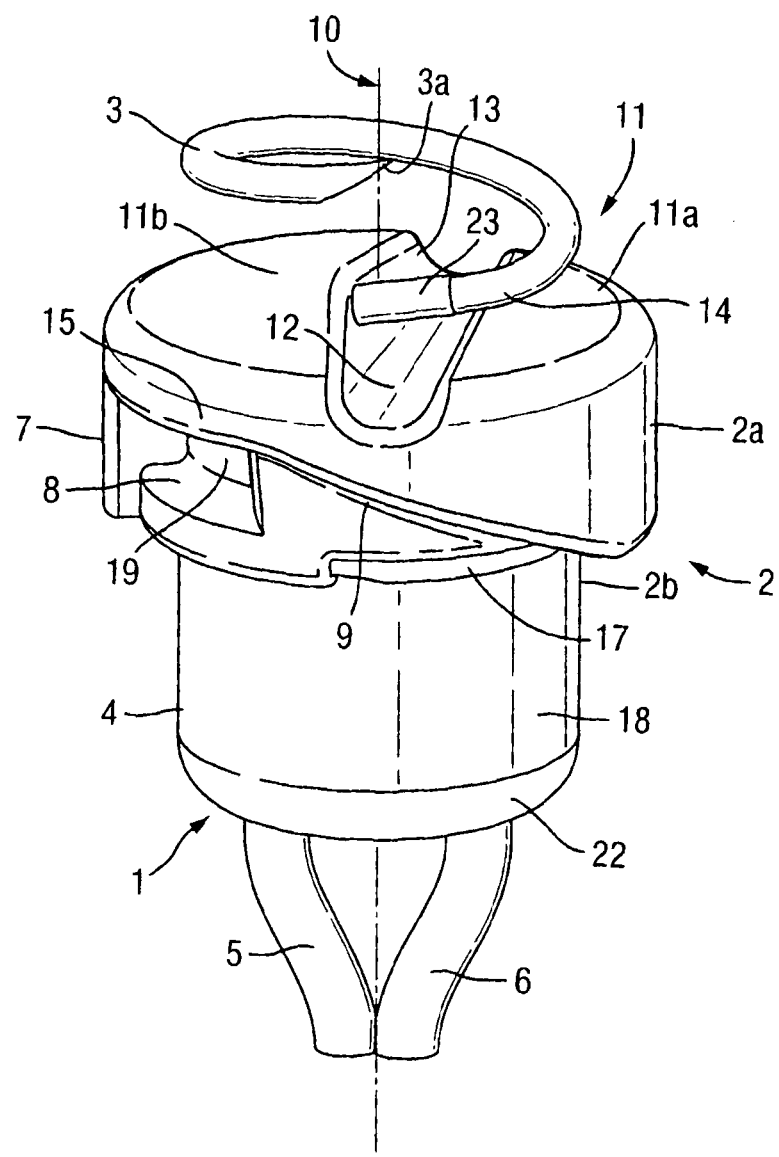
FIG. 3 is a perspective view illustrating a preferred embodiment of the fetal electrode from one side.

The improved fetal scalp electrode 1 illustrated in FIG. 3 has a low profile electrode carrier, i.e., the electrode hub 2. It is made of an insulating material and is designed with only smooth features. The total height of the hub 2 is less than 70% of that of the currently used fetal electrode (see FIG. 7 which shows a comparison of the side elevations).

As shown in FIG. 3 the fetal electrode 1 comprises a smooth, substantially cylindrical body of material which forms the electrode hub 2. In fact the hub 2 is made up from two cylindrical elements; a wider, contact portion 2a with a spiral wire electrode 3 having a sharp tip 3a, and a narrower tail portion 2b including a cylindrical reference (ground) electrode 4 and electrical leads 5, 6.

The spiral wire electrode 3 and cylindrical reference electrode 4 should be made of the same material in order to avoid galvanic corrosion and the associated galvanic currents which can create noise and disturb the fECG signal. In one embodiment the material of the electrodes 3, 4 is a stainless steel. Preferably, the electrodes 3, 4 include an inert coating, for example, the electrodes 3, 4 could be subjected to a passivation process such as treating the stainless steel with a mild oxidant, e.g., a nitric acid solution, to further improve the reliability of the fECG signal.

The wider contact portion 2a includes radial formations in its circumferential wall 7 that are in the form of a substantially rectangular recess 8 and a track 9 which follows a path inclined to the axis 10 extending around the circumferential wall 7 to define a spiral ramp. In the embodiment shown, there are two recesses 8, one on each side of the electrode hub 2. In other embodiments there may be more than two recesses 8, for example, three or four recesses 8.

On the contact face 11, where the spiral wire electrode 3 exits the electrode hub 2, there is provided a smooth transverse groove 12 extending underneath the spiral wire electrode 3. The transverse groove 12 has two functions. The first is to define a wall 13 which is perpendicular to the base portion 14 of the spiral wire electrode 3, the wall 13 extending roughly in the axial and radial directions, and hence substantially at right angles to a radially extending planar segment 11a of the contact face 11. This provides a defined rotational stop on the electrode hub 2, as the planar segment 11a and wall 13 are brought into contact with the fetal epidermis during application of the fetal electrode. The second function of the transverse groove 12 is to prevent the fetal electrode from unwinding. Fetal tissue, during application, expands into the volume of the transverse groove 12 to lock the fetal electrode 1 in position. The transverse groove 12 also allows vernix caseosa to escape from underneath the contact face 11 of the hub 2 during application.

In order to prevent both under and over rotation of the fetal electrode 1 during application, the hub 2 has integrated radial formations in the form of rectangular recesses 8 provided on both sides of the electrode hub 2, that are arranged to disengage from the connecting elements of the torque head 30 provided on the end of the drive tube 31 at a certain level of torque. The torque limiting connection of the drive tube 31 with the fetal electrode 1 is more clearly seen in FIG. 4. The torque head 30 transmits positive drive to the electrode hub 2 up to a predetermined level of torque, for example, 0.01-0.02 Nm. Once this point has been reached, the torque head 30 disengages from the recesses 8 of the electrode hub 2, allowing the drive tube 31 to rotate with respect to the electrode hub 2.

The torque head 30 comprises two flexible prongs 32, each provided with a retaining lug 33 that is configured to engage a recess 8. In addition, the end 34 of the prong 32 abuts against the top edge 15 of the recess 8 in order to transmit axial forces to the electrode hub 2. Once the torque limit is reached, the drive tube 31 moves in a clockwise direction around the hub 2 (viewed from the drive tube end of the fetal electrode 1) with the prongs 32 flexing outwardly to release the retaining lugs 33 from the rectangular recesses 8 in the electrode hub 2. Guided by the track 9, the end 34 of each prong 32 slides around a circumferential surface 16 to an axial ramp 17 and onto the circumferential wall 18 (see FIG. 3) forming the tail portion 2b of the electrode hub 2. The diameter of the tail portion 2b is the same as or smaller than the bottom surfaces 19 of the recesses 8, so that the torque head 30 disengages from the electrode hub 2 easily.

Figure 4:
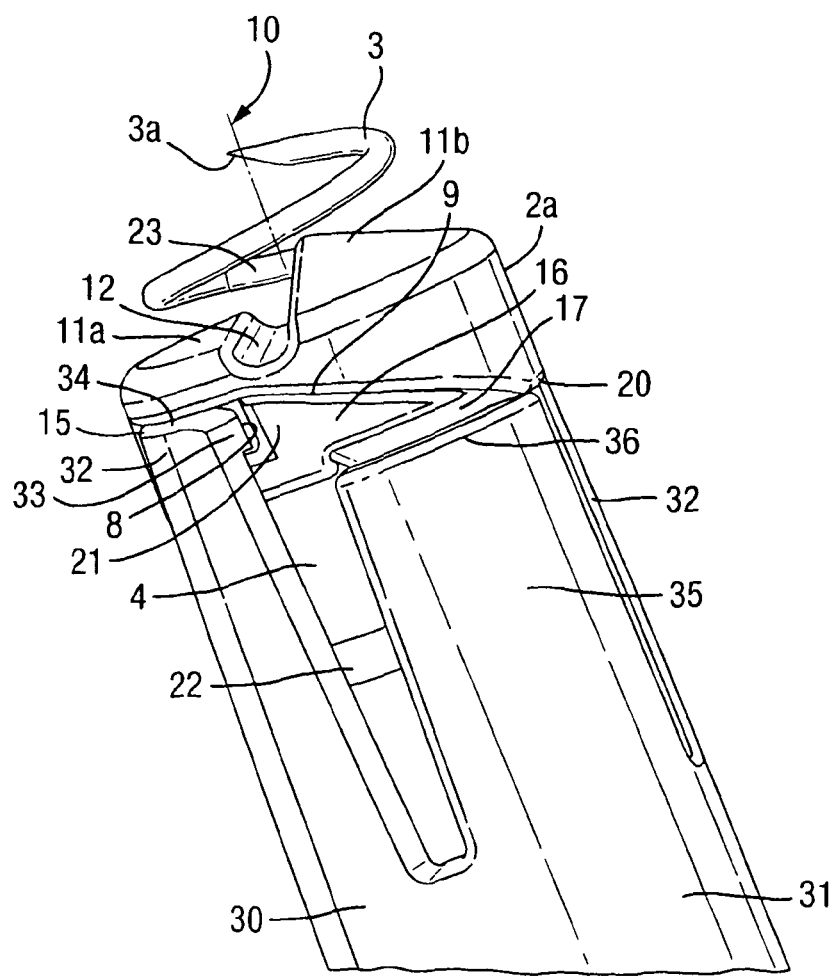
FIG. 4 is a perspective view showing an enlargement of the torque limiting connection in a preferred embodiment, retaining the fetal electrode on an end of the drive tube.

As can be seen in FIG. 4, the track 9 follows a path which is inclined to the axis 10 of the electrode hub 1. Thus, as the distal end 34 of the prong 32 is guided by the track 9, the drive tube 31 is pushed back slightly away from the end of the electrode hub 2 with the contact face 11 and the spiral wire electrode 3. The midwife or operator of the drive tube 31 can detect this small push back into the hand to gauge when the fetal electrode 1 has been correctly fitted and has released from the drive tube 31. The torque head 30 and the deflection surface provided by the track 9 means that the drive tube 31 can be made from a slightly stiffer material than the conventional arrangement, which provides further tactile feedback to help the midwife with applying the fetal electrode 1.

The drive tube 31 is also provided with two further extensions 35 (only one is visible in FIG. 4), which are positioned between the two prongs 32 to help support the sides of the electrode hub 2 whilst it is retained by the torque head 30. The end surface 36 of these extensions 35 abuts against a step 20 between the circumferential surface 16 of the contact portion 2a and the narrower circumferential wall 18 of the tail portion 2b, to help stabilise the connection and also to transmit axial forces to the hub 2. The exit edge 21 of the recess 8 may also be sloped in the direction of rotation to aid disengagement from the torque head 30.

The firm grip of the torque head 30 on the electrode hub 2 prevents the fetal electrode 1 disconnecting prematurely. It also makes the stretching of the electrode wires 5, 6, which is usually required with the prior art fetal electrodes as a way of retaining them on the end of the drive tube when applying torque, is no longer necessary. This means that the electrode wires 5, 6 can remain neatly twisted together, which has benefits in terms of averaging of any interference from electromagnetic sources.

Figure 5:
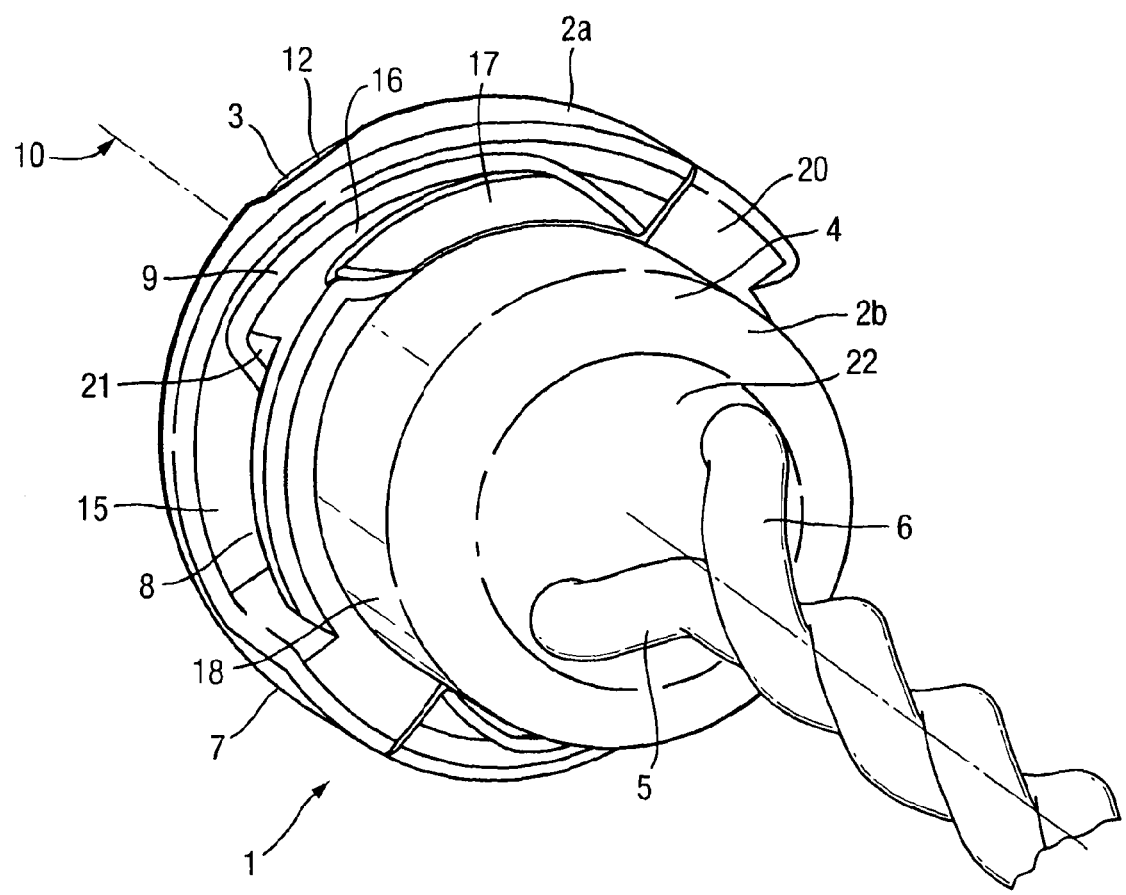
FIG. 5 illustrates a perspective view of the fetal electrode of FIG. 1 looking along the axis of rotation towards the contact face.

FIG. 5 shows a perspective view of the preferred embodiment of the fetal electrode 1 from the underside (the drive tube side), showing the recess 8, its top edge 15 leading into the track 9, which is stepped into the circumferential wall 7 of the contact portion 2a. The circumferential surface 16 leading to axial ramp 17 may also slope inwardly to smooth off the step between the different diameter sizes between the exit edge 21 of recess 8 and the tail portion 2b. This helps the prongs 32 to disengage properly and slide over the respective circumferential surface 16. The narrow diameter of the tail portion 2b can also be seen providing the step 20 for the end surface 36 of one of extensions 35 to abut against. The cylindrical metal sleeve which forms the ground electrode 4, defines the cylindrical wall 18 of the tail portion 2b. The insulating material forming the body of the electrode hub 2 extends through the cylindrical ground electrode 4 to form tail end 22, from which the electrode wires 5, 6 exit to feed electrical signals to a fetal monitor (not shown), usually via a so-called leg-plate connector. At the other end of the hub 2, a portion of the spiral wire electrode 3 is just visible through the mouth of the transverse groove 12 provided in the contact face 11.

Figure 6:
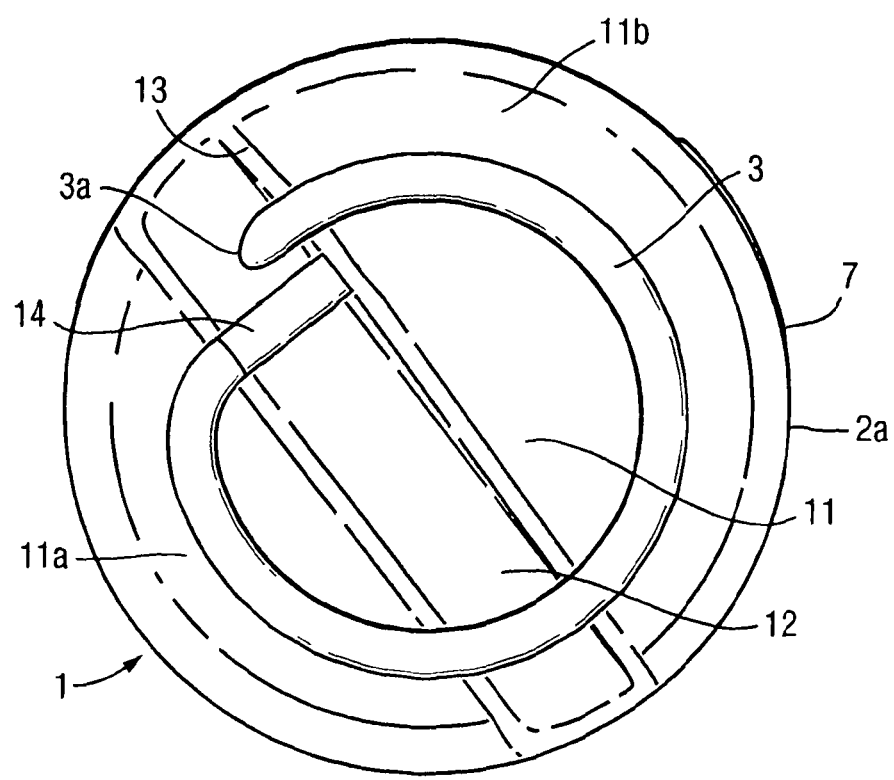
FIG. 6 shows a perspective view of the fetal electrode from the other end and off to one side of the axis.

FIG. 6 shows a view of the fetal electrode 1 looking approximately down the axis 10 towards the contact face 11. The groove 12 extends radially underneath the base portion 14 of the spiral wire electrode 3, across the contact face 11 from one side of the circumferential wall 7 of the contact portion 2a to the other. The groove 12 can be seen extending transversely to this base portion 14. The combination of the transverse groove 12 and the raised exit of the spiral wire electrode 3 from the axially extending wall 13 provide a profile which can grip the fetal tissue after insertion of the spiral wire electrode 3 without unduly trapping fetal hair so that the fetal electrode 1 can be removed easily on application of an unscrewing force by the midwife. In this view it can also be seen how the transverse groove 12 and the planar segment 11a of the contact face 11 together make up a substantially semi-circular area of the contact face 11. The other semi-circular region 11b of the contact face 11 is formed from insulating material which supports the base portion 14 of the spiral wire electrode 3. The raised profile of this region 11b is smoothed off so as not to harm the fetus.

Figure 7A:
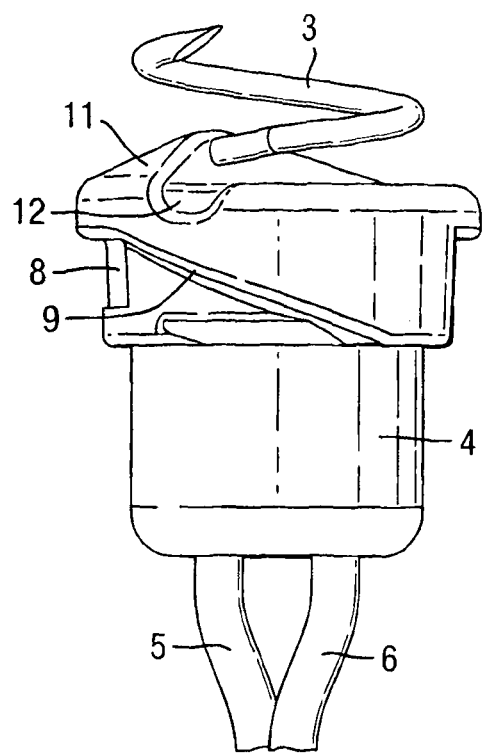
FIG. 7 is a comparison showing the preferred embodiment of the fetal electrode on the left hand side of the image, and a conventional fetal scalp electrode on the right hand side of the image.
Figure 7B:
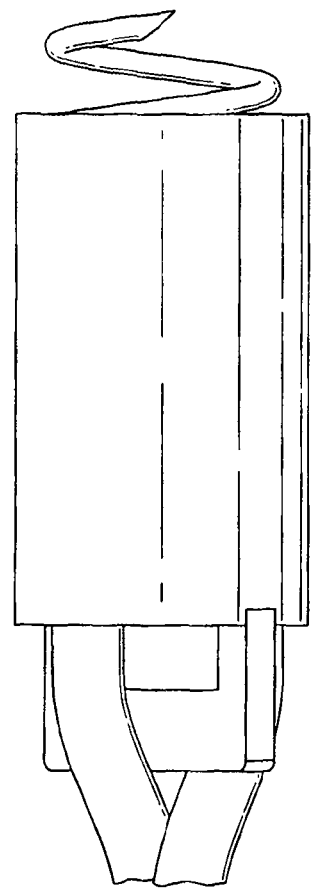

As shown in FIG. 7, the new electrode hub design of the fetal electrode 1 shown on the left hand side of the photograph (fetal electrode (a)) is much more compact than the conventional fetal electrode design (fetal electrode (b)) illustrated on the right of the photograph. The contact face 11 is also wider providing a more stable attachment, and the reduced height means that there is less leverage exerted on the electrode hub 2 during labour. In the examples shown, the contact face 11 is 7.5 mm diameter, the fetal electrode 1 has a height excluding the spiral wire electrode 3 of 7 mm and the tail portion 2b has a diameter of 5.5 mm. This compares to conventional fetal electrodes where the height excluding the spiral wire electrode would be around 12 mm and the maximum diameter would be around 5.5 mm. The lower profile and larger base area, prevents electrode from overturning due to an excessive long lever of an extended electrode hub. An overturned fetal electrode 1 during labour might result in the sharp spiral tip 3a being pressed out from fetal epidermis, resulting in vaginal lacerations. Also as is shown in FIG. 6, the lower profile hub design means that the spiral wire electrode 3 can be arranged more inbound on the contact face 11 of the hub 2. In other words, there is a larger distance from outer circumference of the spiral wire electrode 3, especially the sharpened tip 3a, to the circumferential wall 7, compared to current available fetal electrodes. The larger distance functions as a guard, further protecting maternal tissue in case of an overturned electrode resulting in an exposed spiral tip 3a.

Figure 9:
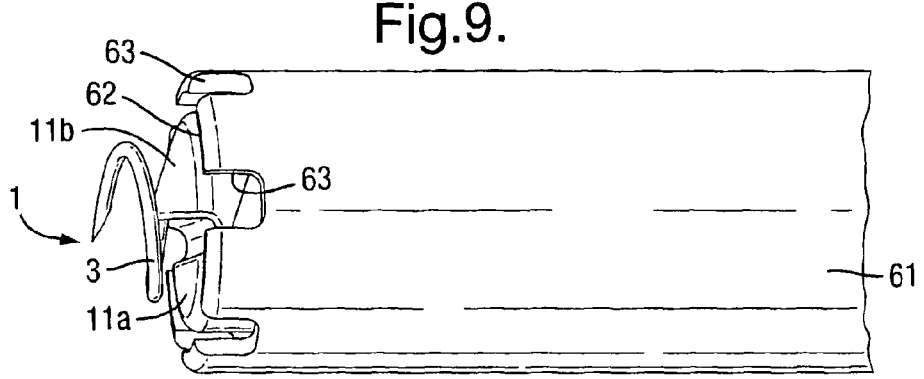
FIG. 9 shows an enlargement of a preferred fetal electrode held within a guide tube.

As can be seen from FIG. 4, the external diameter of the drive tube 31 corresponds substantially to that of the contact portion 2a of the electrode hub 2 so that when the fetal electrode 1 is being held by the torque head 30, the components provide a smooth profile which can be accommodated within a guide tube (see also FIGS. 8a, 8b and 9).

In the electrode assembly 60 illustrated in FIGS. 8a and 8b, the connected drive tube 31 and fetal electrode 1 are housed within a guide tube 61. The distal end 62 of the guide tube 61 is formed as a crowned tip having a series of short slots or notches 63 extending in the axial direction (see FIG. 9). This crowned tip 62 enables the midwife to maintain the position of the guide tube 61 more easily during application of the spiral electrode onto the slippery surface of the fetal head. In order to screw in the fetal electrode 1 efficiently, it is important to keep the guide tube 61 stationary in order to avoid it rotating eccentrically about the end of the spiral wire electrode 3. To facilitate this, the crowned tip 62 allows excessive amounts of vernix caseosa to escape through the slots or notches 63 as the fetal electrode 1 is brought close to the fetal epidermis during application.

Figure 10:
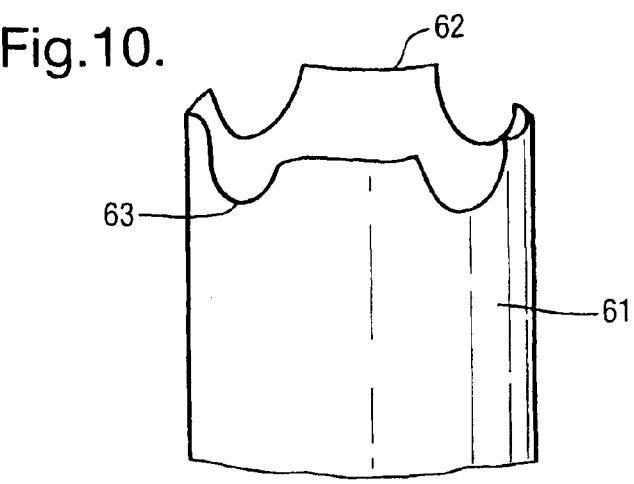
FIG. 10 illustrates an alternative notch arrangement in the guide tube.

FIG. 10 shows an alternative form for the crowned tip 62 of the guide tube 61. In this embodiment, semi-circular notches 63 have been cut or stamped from the circumferential edge of the guide tube 61. The circular symmetry can help to control and avoid possible sharp regions forming at the edges of a notch 63. In another embodiment (not shown) the notches are triangular, creating an inverted saw-tooth pattern. The notches 63 should be sufficiently shallow to prevent impeding the rotation of the drive tube 31 and the fetal electrode 1, and notches of around 1 mm deep or smaller have been found to work well. Also in the case of curved notches or triangular notches 63, where the sides of the notches 63 are sloped with respect to the axis of rotation 10, it further helps to prevent the drive tube 31 or electrode hub 2 from becoming caught.

FIG. 8a illustrates the electrode assembly 60 in a ready-to-use configuration. FIG. 8b shows an exploded view of the components, illustrating the fetal electrode 1 connected by the twined electrode leads 5, 6 to an electrode connector plug 64. On route to the connector plug 64, the electrode wires 5, 6 pass through holes 51, 52 of a shuttle 50. The purpose of this shuttle 50 will be explained below. A torque head 30 attaches to the hollow drive tube 31 for connection to the electrode hub 2. The torque head 30 comprises a ring member having the prongs 32 and extensions 35 extending axially therefrom, the torque head 30 resembling a crown that fits on the end of the drive tube 31. If preferred, the crowned tip 62 could be formed by cutting or punching out slots or notches 63 from the material of the drive tube 31 itself. The electrode wires 5, 6 and the shuttle 50 pass up the inside of the drive tube 31 in the assembly 60 of FIG. 8a. The drive tube 31 and the connected electrode hub 1 are then housed within a hollow guide tube 61, with the tip 3a of the spiral wire electrode 3 just protruding out beyond the crowned tip 62 of the guide tube 61. A handle 65 is fitted to the other end of the drive tube 31 for the midwife to manipulate during application of the fetal electrode 1.

One advantage with using a torque limiting connection is that the drive tube 31 and in particular the guide tube 61 can be made stiffer, providing additional tactile feedback to the midwife. As shown in FIG. 8a, the guide tube 61 is bent in a middle section 61a to provide a better anatomical fit. However, the bend causes the drive tube 31 and guide tube 61 to rub against each other. While there may be some lubrication through the presence of bodily fluids, preferably friction between the components is further minimised by treating a portion of the internal surface of the guide tube 61 with a lubricating coating. Such a coating may be formed of silicone or some other low friction providing material. Preferably the coating does not extend the entire length of the guide tube 61, for example, the coating may extend for a length of 5 to 10 cm. In an alternative embodiment (not shown) a middle section of the exterior of the drive tube 31 is provided with a lubricating coating, such as a silicone coating. Again this is preferred not to extend the entire length of the drive tube 31 in case it interferes with the push-fit connection of the handle 65 or the torque head 30.

Figure 11:
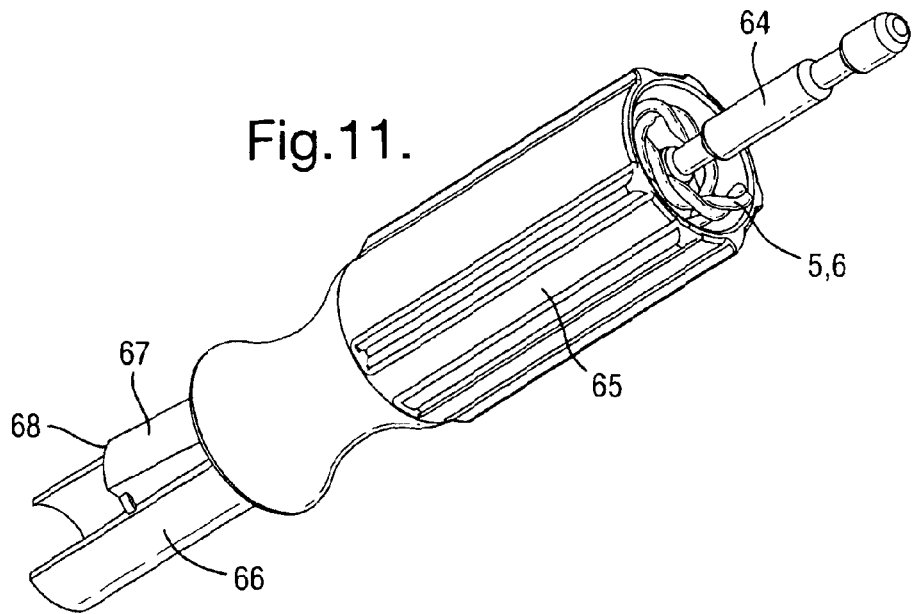
FIG. 11 illustrates a perspective view of the end of a preferred handle for the drive tube, showing the electrode wires and connector in a storage configuration.

As shown in FIG. 11, the handle 65 is hollow and provides a large cavity for housing the coiled up electrode wires 5, 6 until the fetal electrode 1 has been correctly fitted. As shown, the electrode connector plug 64 is held partially projecting from the end of the handle 65 so that it can be pulled out and plugged into a connecting device, such as a leg-plate connector, once the fetal electrode 1 is in place on the fetus. This arrangement has two significant advantages. Firstly the slippery fetal epidermis can make it difficult to keep the guide tube 61 fixed on the fetal head while rotating the handle 65 on the drive tube 31 of the scalp electrode assembly 60. With conventional arrangements, the electrode wires would normally hang out of the rear of the handle by about 30 cm and this can make the procedure even more difficult as the wire can become tangled around the wrist of the midwife. Also, the electrode wires hanging out from the end of the handle will bend to hang vertically, with the result that the electrode wires will rub against the edge of the handle and oppose the rotation, and to some extent can also unscrew the electrode while the midwife is changing grip. Therefore, by providing a hollow handle 65 defining a housing which can accommodate the electrode wires 5, 6 until the fetal electrode 1 has been correctly positioned, it means that the midwife will benefit from the larger diameter grip and the electrode wires will be kept out of harms way. This has benefits independent of many of the features described above and therefore, in accordance with a further aspect, the present invention provides an electrode assembly including a fetal electrode which is connected to a drive tube, the fetal electrode being a bipolar device and having two electrode wires extending therefrom to convey electrical signals from two electrodes provided on an electrode hub, the electrode wires extending within the drive tube to a handle, wherein the handle includes a cavity which retains a portion of the electrode wires in a coiled up configuration and at least one end of an electrode connector plug connected to the electrode wires, within a grip portion of the handle. The portion of the electrode wires 5, 6 coiled up within the handle preferably represents more than 40% of their length, more preferably more than 50% of their length.

As shown in FIG. 11, the handle 65 includes a part-cylindrical bushing 66 which fits within the drive tube 31. Within a cut-away region of the bushing 66, there is provided a stop member 67 which is biased to project outwardly beyond the radius of the drive tube 31 in order to engage the end of the guide tube 61 with an abutment surface 68. The stop member 67 helps to keep the sharp tip 3a of the spiral wire electrode 3 within the protection of the guide tube 61 during transportation. This in turn helps to prevent a protective pouch, which is used to keep the assembly sterile, from being punctured prior to use. The retracted sharp tip 3a is also maintained out of harms way right up to the point where the guide tube 61 has made contact with the fetus and the fetal electrode 1 is deployed.

The removal of fetal scalp electrodes is a neglected area in the design of such electrodes. In about 10% of all births, i.e., not that uncommon, a suspected bad fetal outcome leads to an emergency caesarean section. In these situations, the electrode needs to be removed quickly and in a sterile manner prior to intervention. If the fetus is high up in the birth canal, the electrode is difficult to reach, and there is a chance of causing infection when trying to reach and unscrew the fetal electrode. It has become clinical practice in such a situation, contrary to manufacturers' instructions, to instead cut the electrode wires, separate the wires and then gently pull them apart. If done correctly, the direction of the two twined separate wires will lead to the fetal electrode unscrewing itself. The hazard lies in that one should never try to pull out the electrode straight out, and that an electrode of the conventional style might be more or less stuck to the fetal head.

Figure 12A:
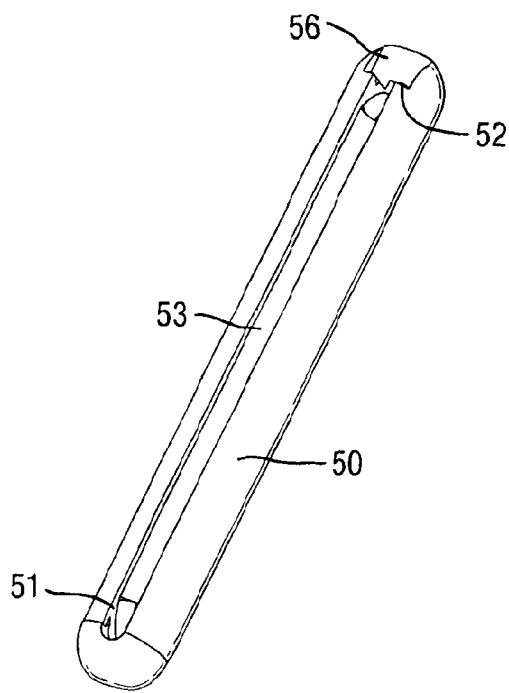
FIGS. 12a and 12b show front and rear perspective views of a preferred shuttle.
Figure 12B:
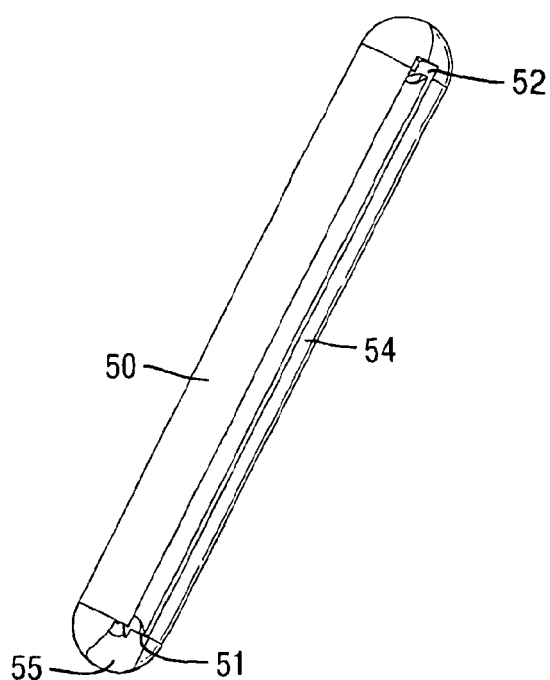
Figure 13:
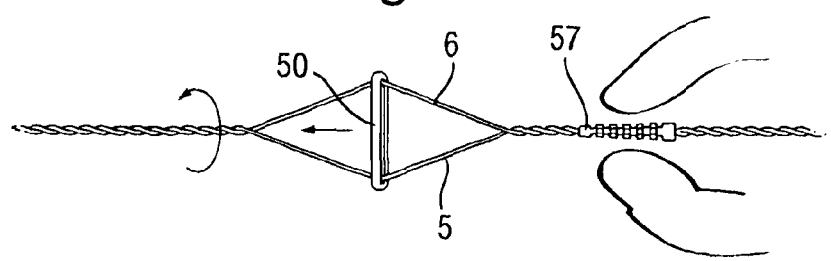
FIG. 13 shows a schematic view of the shuttle of FIGS. 12a and 12b being used to unwind the electrode wires leading to the electrode hub.
Figure 14:
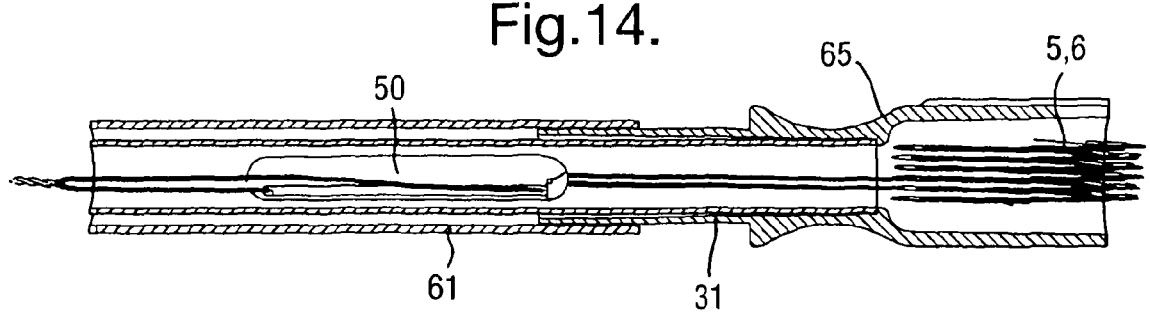
FIG. 14 illustrates a cross-sectional view showing the preferred storage configuration of the shuttle and electrode wires within the drive tube and handle, with the drive tube extending within the guide tube.

In a preferred embodiment, the electrode wires 5, 6 are provided with a shuttle 50 as shown in FIGS. 12a, 12b and 13. The shuttle 50 comprises an elongate, cylindrical member which is around 20-30 mm long having a hole 51, 52, one for each electrode wire 5, 6, provided at each end. On either side of the shuttle 50, a longitudinal groove 53, 54 is provided, each groove extending from one of the holes 51, 52 to a mouth 55, 56 at the respective opposite end of the shuttle 50. The longitudinal grooves 53, 54 are sized to accommodate the electrode wires 5, 6, and in this way provide a compact arrangement when stored within the drive tube 31 as shown in FIG. 14. Thus the shuttle 50 provides a midwife with a ready tool, with which she can unscrew the fetal electrode 1 in a controlled way, by holding the electrode wires 5, 6 still with one hand, while sliding the shuttle 50 forward towards the fetus, and thereby imposing a rotational force on the fetal electrode 1 to unscrew it. A moulded grip 57 may be provided on the electrode wires 5, 6 to help twist them, or to provide a firm grip of the wires while executing the removal procedure described above.

Apart from the anatomical advantages, the new electrode hub design also permits efficient manufacturing, since it can be directly moulded from an injection mould consisting of two halves. During this process, it is possible to apply a coating of insulating material 23 (see FIG. 3) to the base portion 14 of the spiral wire electrode 3. The advantage of this is that it isolates the spiral wire electrode 3 from possible contact with non-fetal tissue and amniotic fluid, thereby maximising the fECG signal amplitude and minimising movement artefacts. In the arrangement shown in FIG. 3, the isolation coating 23 may extend about 1 mm beyond the wall 13 of the electrode hub 2. Greater isolation coating lengths can be used if a larger safety margin is required. While this type of isolating coating can be used on conventional fetal electrodes, the benefit to their operation is harder to achieve from a manufacturing standpoint because of the design of the spiral wire electrode and hub in the conventional arrangements. The most effective way of providing this partial isolation 23 is to coat the base portion 14 of the spiral electrode wire 3 during the moulding phase. However this can still be quite difficult to achieve due to the small dimensions, since the thickness is of the order of 0.1 mm. Therefore, to make it easier to apply the coating 23 of isolating material during moulding, the base portion 14 of the spiral wire electrode 3 is preferably straight for the first few millimetres of the electrode's length in order to allow for easier closing of the mould halves. It is also possible to provide the base portion 14 of the spiral wire electrode 3 with an isolating coating 23 using isolating varnish, or through coating with an isolating oxide by means of a physical vapour deposition (PVD) process, and such an isolating coating may also have the advantage of being thinner.

Figure 15:
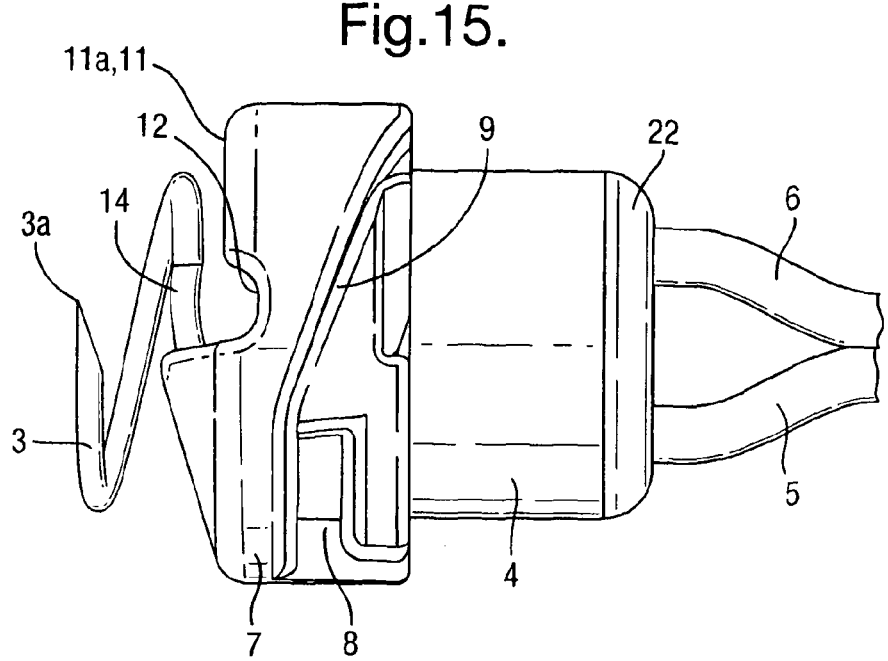
FIG. 15 shows an image of a further embodiment of the fetal electrode.

FIG. 15 shows an image of a further embodiment of the fetal electrode 1, where after injection moulding, the base portion 14 (the straight section) of the spiral wire electrode 3 is then kinked, so that part of the base portion 14 extends approximately parallel to the planar segment 11a of the contact face 11 or even slightly towards it. This creates a region of zero or negative pitch in the spiral wire electrode 3 which can grip the fetal tissue against the contact face 11. The region of zero or negative pitch extends across the transverse groove 12 as shown and may account for the first 2 mm of the spiral wire electrode 3. The kink in the base portion can be formed while cutting off waste material left over from the injection mould channels.

Figure 16:
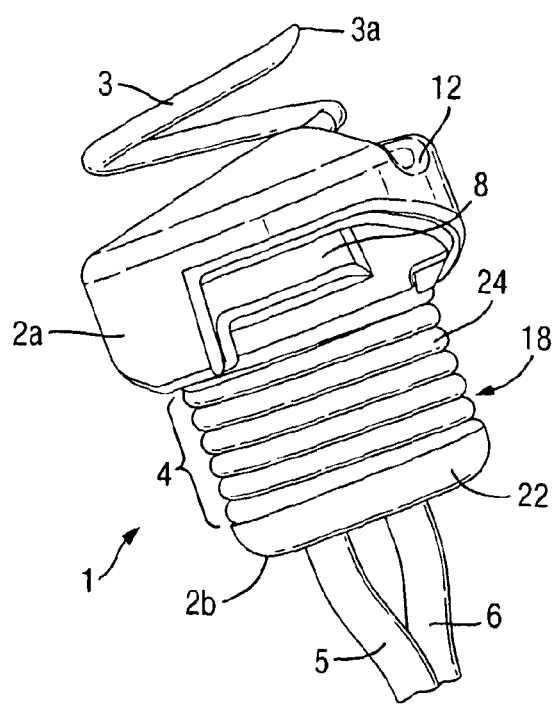
FIG. 16 shows a side view of a further preferred embodiment of the fetal scalp electrode.
Figure 17:
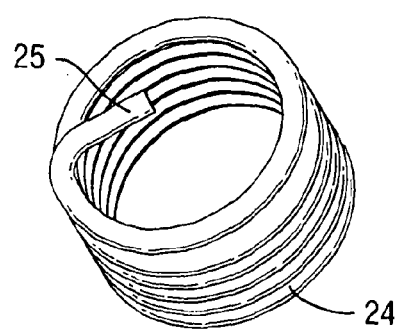
FIG. 17 is a perspective view of a coiled wire that can be used as the reference electrode in the embodiment of FIG. 16.

Another preferred embodiment of the fetal electrode 1 is illustrated in FIG. 16. The contact portion 2a with the spiral wire electrode 3 is the same as the first embodiment illustrated in FIG. 3. The same reference numerals are used for the corresponding parts in FIG. 16 and do not require further explanation here. The tail portion 2b, however, is made differently to the embodiment in FIG. 3, namely that the ground electrode 4 is made from a coiled wire 24 that is shown in more detail in FIG. 17. As shown, the coiled wire 24 corresponds in shape and function to the cylindrical metal sleeve that forms the ground electrode 4 in FIG. 3 and defines the cylindrical wall 18 of the tail portion 2b. Forming a ground electrode 4 from a coiled wire 24 has been found to offer several advantages. Firstly, the end of the wire 25 can be arranged to project inwardly of the hub 2, so that when an electrode wire 5, 6 is welded to the end 25 of the wire 24 during manufacturing, the weld point is then later encapsulated within the moulded plastic material of the hub 2 in the final product. Hence any damage that is caused to the outer surface of the reference electrode 4 during the welding operation, will be hidden deep within the plastic material of the hub 2 and therefore will not affect the electrical properties of the fetal scalp electrode 1. In other words, any noise generation in the signal will be minimised and a better recording of the fECG signal can be achieved. In addition, the conductive part of the electrode leads 5, 6 that is connected to the end 25 of the wire 24, will generally not be made of the same inert material as the ground electrode 4. For example, typically it might be made of copper or tinned copper. By forming the finished fetal scalp electrode 1 with the end of the electrical leads 5, 6 encapsulated within the moulded plastic material of the hub 2, there is a greater chance that this part will be completely isolated, again reducing the possible noise component to the fECG signal. There is also less risk that the insulation that isolates these parts will fail. Excessive noise can result from corrosion and, in a worse case scenario, may even result in the monitor detecting a signal similar to the fetal ECG and presenting this as a false trace. Consequently, ensuring that these parts are completely isolated within the hub 2 leads to a more reliable product. Preferably the wire 24 is coiled tightly as shown in FIGS. 16 and 17 in order to replicate the form of the cylindrical sleeve provided in FIG. 3 and avoid the creation of possible gaps into the hub 2. However, it would also be possible to use a slightly wider spacing between the helical turns if so desired, but this would tend to increase the length of the fetal electrode 1 for a given surface area of ground electrode 4. The wire 24 may be of any cross-sectional profile, and is preferably of circular cross-section in order to avoid creating any sharp edges that might cause injury to the mother or fetus. The fetal electrode 1 shown in FIG. 16 can be used in conjunction with any of the above-described embodiments of the electrode assembly comprising the fetal electrode 1 attached to a drive tube 31, for example, as shown in FIGS. 8a and 8b. The remainder of the tail portion 2b is the same as the FIG. 3 embodiment.

Although the invention above has been described in connection with preferred embodiments of the invention, it will be evident for a person skilled in the art that several modifications are conceivable without departing from the invention as defined by the following claims.

What is clamed is:

1. An electrode assembly comprising a fetal electrode and a drive tube, the fetal electrode having an electrode hub with a spiral wire electrode provided on one end, the fetal electrode being connected to the drive tube by a torque limiting connection, the connection allowing the drive tube to separate from the electrode hub and to continue to turn with respect to the electrode hub once a predetermined torque has been reached, wherein the electrode hub is provided with a deflection surface to deflect the drive tube in a direction away from the end of the hub with the spiral wire electrode as rotation of the drive tube continues beyond the point of disconnection.

2. The electrode assembly as claimed in claim 1, wherein the electrode hub comprises a substantially cylindrical body and the deflection surface is in the form of a track provided in a circumferential surface and encircling a portion of the electrode hub.

3. The electrode assembly as claimed in claim 2, wherein two tracks are provided, one on each side of the electrode hub.

4. The electrode assembly as claimed in claim 2, wherein one or more recesses are provided in the circumferential surface of the electrode hub, each for engagement by a retaining lug of a prong provided on the drive tube, the one or more prongs forming a torque limiting connection with the one or more recesses.

5. The electrode assembly as claimed in claim 1, wherein the deflection surface is a track inclined between 40 and 80° to an axis of rotation of the electrode hub.

6. The electrode assembly as claimed in claim 5, wherein the track follows a path of constant pitch which is inclined at 70° to the axis of rotation of the electrode hub.

7. The electrode assembly as claimed in claim 1, wherein the drive tube has a torque head which forms the torque limiting connection with the fetal electrode, the torque head comprising two longitudinally extending prongs, each with a retaining lug provided on a distal end, and two further extensions provided between the prongs arranged to grip an end of the fetal electrode.

8. The electrode assembly as claimed in claim 1, wherein the end of the electrode hub which is intended to contact the fetus, has a contact face that is provided with a groove, which extends transversely to a base portion of the spiral wire electrode.

9. The electrode assembly as claimed in claim 8, wherein the contact face comprises, along one edge of the groove, a planar segment that extends in a plane which is substantially perpendicular to an axis of rotation of the electrode hub, and along the other edge of the groove, a wall which extends substantially parallel to the axis of rotation, the planar segment and the wall arranged so that they come into contact with the fetus only once the spiral wire electrode has been fully inserted.

10. The electrode assembly as claimed in claim 9, wherein the spiral wire electrode exits the contact face of the electrode hub from the wall at a position spaced axially from the planar segment.

11. The electrode assembly as claimed in claim 8, wherein the base portion of the spiral wire electrode is straight.

12. The electrode assembly as claimed in claim 11, wherein the base portion of the spiral wire electrode includes a coating of an insulating material that extends from where the spiral wire electrode exits a wall of the contact face a distance of 1 mm or further along the spiral wire electrode.

13. The electrode assembly as claimed in claim 8, wherein the base portion of the spiral wire electrode extends perpendicularly to a hub axis and includes a region where the spiral wire electrode has been kinked to extend parallel to or towards a planar segment of the contact face.

14. The electrode assembly as claimed in claim 1, wherein the drive tube is housed within a guide tube and an end of the guide tube adjacent the fetal electrode is provided with a series of notches.

15. The electrode assembly as claimed in claim 14, wherein an inner portion of the guide tube and/or external portion of the drive tube has been pre-treated with a lubricating coating.

16. The electrode assembly as claimed in claim 1, wherein the electrode hub of the fetal electrode comprises two cylindrical elements of different diameter that are axially aligned to form a substantially cylindrical body, with the spiral wire electrode extending from the larger diameter cylindrical element and a cylindrical metal sleeve provided on the narrower diameter element to form a ground electrode, the fetal electrode further comprising a pair of electrode wires exiting from an end of the narrower diameter cylindrical element.

17. The electrode assembly as claimed in claim 16, wherein the cylindrical metal sleeve of the ground electrode is formed by a coiled wire.

18. The electrode assembly as claimed in claim 17, wherein an end of the coiled wire extends into the electrode hub for connection to one of the electrode wires.

19. The electrode assembly as claimed in claim 16, wherein the diameter of the larger diameter cylindrical element is about 7.5 mm and the axial height of the two cylindrical elements forming the electrode hub is about 7 mm.

20. The electrode assembly as claimed in claim 16, wherein the drive tube is provided with a handle which includes a cavity for housing the electrode wires and at least a portion of an electrode connector plug until the fetal electrode has been deployed.

21. The electrode assembly as claimed in claim 16, wherein the electrode assembly further includes a shuttle, which is in the form of an elongate member having a hole at each end, with one of the electrode wires passing through one hole and the other electrode wire passing through the other, wherein the shuttle is housed within the drive tube between the fetal electrode and the handle.

22. A fetal electrode comprising a substantially cylindrical electrode hub with a spiral wire electrode extending from one end, wherein the surface of the electrode hub is provided with formations for connecting to an end of a drive tube to drive the electrode hub about an axis of rotation, the formations providing a positive connection for transmitting drive up to a limited level of torque, and wherein the electrode hub also includes a deflection surface in the form of a track which is for deflecting the drive tube in an axial direction away from the end of the electrode hub having the spiral wire electrode once the torque limiting connection has become disconnected.

* * * * *